(12) United States Patent
Thompson et al.

(10) Patent No.: US 6,475,442 B1
(45) Date of Patent: Nov. 5, 2002

(54) KIT FOR USE IN DETECTING GASTRIC DAMAGE

(75) Inventors: Glenn L. Thompson, Waterdown (CA); Dan Giampuzzi, Missisauga (CA)

(73) Assignee: G. D. Searle & Co., Chicago, IL (US)

( * ) Notice: Subject to any disclaimer, the term of this patent is extended or adjusted under 35 U.S.C. 154(b) by 0 days.

(21) Appl. No.: 09/038,688

(22) Filed: Mar. 9, 1998

(51) Int. Cl.[7] .................................................. B01L 3/00

(52) U.S. Cl. ........................ 422/102; 422/61; 436/811; 220/8; 220/666

(58) Field of Search ...................... 422/61, 102; 436/64, 436/94, 811, 813; 220/8, 666, 529; 222/382

(56) References Cited

U.S. PATENT DOCUMENTS

| | | | | |
|---|---|---|---|---|
| 3,754,864 A | * | 8/1973 | Gindler | 23/230 |
| 4,203,967 A | * | 5/1980 | Torres | 424/9 |
| 5,342,330 A | * | 8/1994 | Kane et al. | 604/329 |
| 5,605,840 A | | 2/1997 | Meddings et al. | 436/94 |
| 5,620,899 A | | 4/1997 | Meddings et al. | 436/63 |
| 5,711,445 A | * | 1/1998 | Robbins | 220/8 |

OTHER PUBLICATIONS

Sekin, S., "Enzymatic Determination of Glucose, Fructose, and Sucrose in Tobacco", Tobacco International, vol. 181, Jul. 1979, pp. 27–29.

* cited by examiner

*Primary Examiner*—Lyle A. Alexander
(74) *Attorney, Agent, or Firm*—Fitzpatrick, Cella, Harper & Scinto

(57) ABSTRACT

This invention provides a kit for use in a method for detecting gastric damage. The kit comprises: (a) a sealed container of sterilized buffered aqueous sucrose solution; and (b) a urine collection device suitable for collection and storage of human urine.

16 Claims, 1 Drawing Sheet

KIT FOR USE IN DETECTING GASTRIC DAMAGE

BACKGROUND OF THE INVENTION

1. Field of the Invention

This invention relates to a kit that is useful in connection with a method for the non-invasive detection of gastric damage. The kit contains a sealed container of a buffered aqueous solution of sucrose that is advantageously storage stable and a urine collection device.

2. Related Background Art

Stomach ulcers can pose a serious health threat as, in many instances, ulcers are asymptomatic. Since stomach ulcers can develop and be present without any symptoms, the damage brought about by ulcers to the stomach and the bleeding associated with such ulcers can be a serious, and possibly fatal health risk.

Traditional methods for detecting gastric ulcers include endoscopy, barium meal followed by x-rays, and radiolabeled detecting agents. Endoscopy causes patient discomfort, requires anesthesia, and must generally be performed in a clinic or a hospital. X-rays and radiolabeled detecting agents have the common disadvantage of exposing the patient to radiation. In addition, all of these procedures require a skilled evaluation of the results in order to properly diagnose the patient's condition.

A method for detection of gastric epithelial damage, particularly ulcers and lesions in the stomach, using non-invasive, non-radioactive and non-x-ray techniques or procedures is disclosed in U.S. Pat. No. 5,620,899. The method of this reference employs a disaccharide which can be orally administered to a patient, which does not transport across cell membranes, which is metabolized within the small intestine to its monosaccharide components, and which is not broken down elsewhere in the body. Damage to the gastric epithelium will allow the disaccharide to enter the blood without being metabolized. Hence, the disaccharide will appear in the blood or urine to an extent that can be correlated with the extent of gastric epithelial damage. Typically, the disaccharide is administered to a patient, followed by collection of blood or urine, which is assayed for the disaccharide. The use of sucrose in particular as a diagnostic marker in detection of gastric epithelial damage is described in U.S. patent application Ser. No. 08/456,203.

In connection with the method of U.S. Pat. No. 5,620,899 a kit for use by the patient, and containing a buffered aqueous sucrose solution and a urine collection vessel, would be useful.

SUMMARY OF THE INVENTION

This invention is directed to a kit for use in a method for detecting gastric damage. The kit comprises: (a) a sealed container of sterilized buffered aqueous sucrose solution; and (b) a urine collection device that is suitable for collection and storage of human urine.

BRIEF DESCRIPTION OF THE DRAWING

The drawing is a perspective view of a preferred embodiment of the kit.

DETAILED DESCRIPTION OF THE INVENTION

Figure 1:
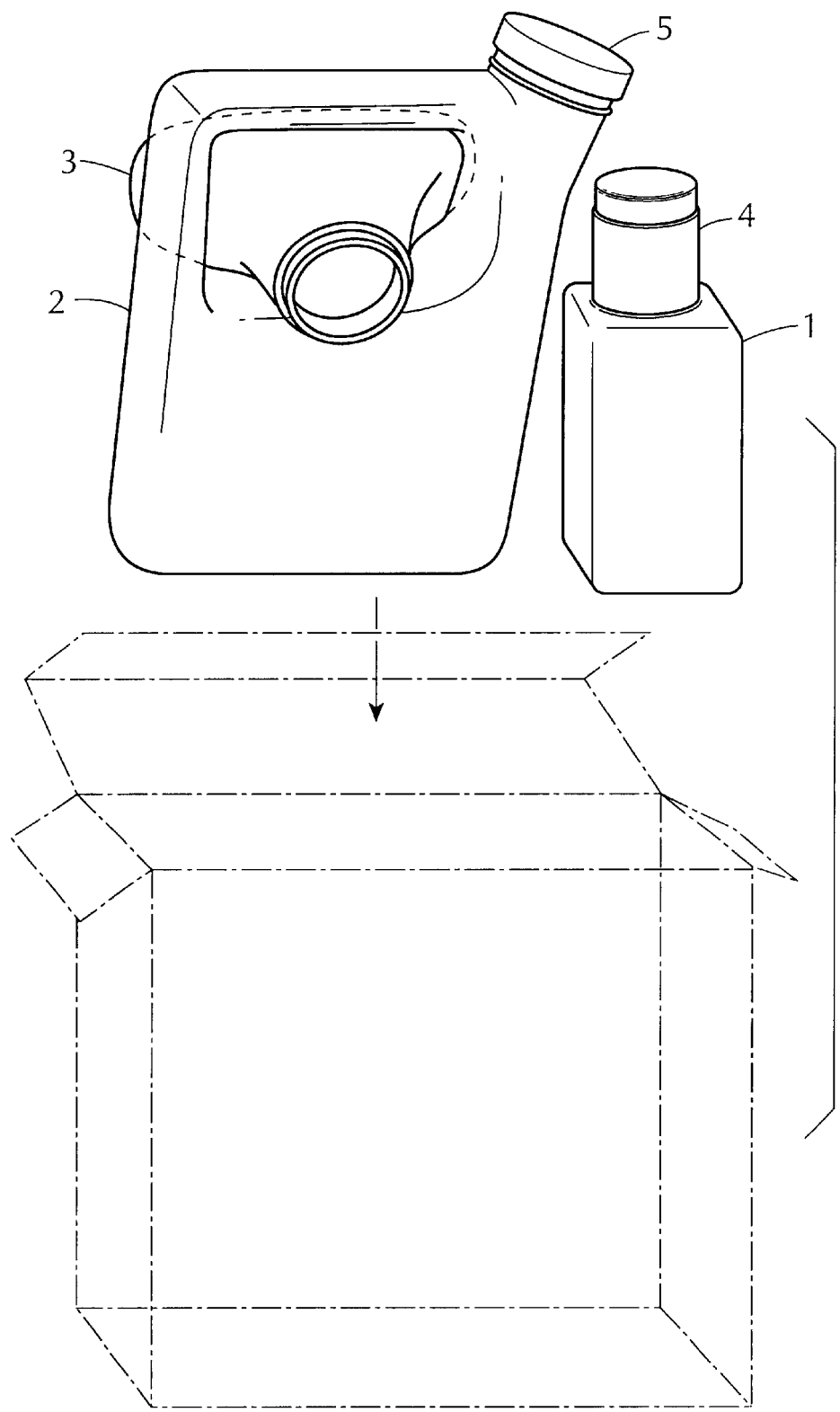

The drawing shows a preferred embodiment of the kit of this invention. The sealed container of aqueous sucrose solution is a plastic bottle 1 and the urine collection device is a plastic container 2. Bottle 1 has a bottle top 4 and container 2 has a threaded cap 5. A funnel 3 is packed together with the container 2. The funnel has a lid (not shown) which fits over the wider end of the funnel. All of these items may be packaged in a single box (dashed lines).

The kit of this invention is intended for use by a patient in connection with a method for detecting gastric damage such as described, for example, in U.S. Pat. No. 5,620,899, the disclosure of which is incorporated by reference herein. The kit provides a patient with a sealed container of sterilized buffered aqueous sucrose solution and a urine collection device. The sucrose solution is described in copending U.S. patent application [Attorney Docket No. 2046.68] entitled "Sterilized Buffered Sucrose Solution for Use in Detecting Gastric Damage", filed contemporaneously herewith, and the disclosure of which is incorporated by reference herein. The patient is instructed to drink the sucrose solution after a sufficient fast period. Urine is then collected and stored in the urine collection device by the patient. The urine is later assayed to determine its sucrose concentration. The sucrose solution ingested by the patient must contain a concentration of sucrose sufficient to allow detection of sucrose in the urine of a patient having gastric damage after administration thereto. Generally, a suitable concentration of sucrose in the solution of this invention is in the range from about 15% to about 25% by weight of the solution, preferably from about 17.5% to about 23.5% by weight of the solution, and most preferably from about 19% to about 21% by weight of the solution.

The solution provided in the sealed container is sterilized to substantially prevent growth of microorganisms in the sucrose solution. The most preferred means for sterilization is heating. The sterilization is conducted by exposing the aqueous sucrose solution to heat at a temperature and for a time that results in effective microbial kill. Such time and temperature, e.g., 121° C. for 8 to 16 minutes, may be readily determined by those skilled in the art without undue experimentation. Heat sterilization, however, of an aqueous sucrose solution is known to cause degradation of the sucrose by inversion to glucose and fructose. Substantial degradation of this nature is deleterious if the aqueous solution is to be employed in the previously described method for detection of gastric damage. It has been advantageously discovered, however, that buffering a sucrose solution in the pH range from about 6 to about 8 will substantially prevent degradation of the sucrose under the conditions encountered during heat sterilization. Preferably, the solution is buffered in the range from about 6.5 to about 7.5, most preferably about 6.8 to about 7.2. An exemplary buffer for use in this invention is dibasic sodium phosphate in combination with citric acid. However, any buffers may be employed that maintain the desired pH of the solution without deleteriously affecting the sucrose content of the solution. Other potential buffer systems include sodium citrate dihydrate in combination with citric acid. The most preferred buffer is dibasic sodium phosphate in combination with citric acid. The amount of buffer must be sufficient to maintain the pH in the desired range. Generally, the amount of buffer is in the range from about 0.01% to about 0.4% by weight of the solution, preferably from about 0.03% to about 0.3% by weight of the solution. The solution of this invention also contains water. Purified water or water for injection may be used.

The sealed container is filled with the buffered sucrose solution and is constructed from a material compatible with aqueous sucrose, the buffers used in the solution, and any other additives employed in the sucrose solution. The container may take the form of a bottle, can, carton, an aseptic package or the like. A particularly preferred container is a bottle constructed of polypropylene. A bottle containing the buffered sucrose solution may be constructed of other materials, e.g., glass, polyethylene, poly(ethylene terephthalate), and the like. The container must be of sufficient volume to contain the amount of solution required to be ingested by the patient in the method for detecting gastric damage. Preferably, the container is of sufficient volume to contain about 450 ml of solution. The container is sealed to prevent the sucrose solution from leaking out of the container. This may be accomplished by a separate component, e.g., a bottle top, cap, or sealing film, or an integral part of the container, e.g., a pop top or the container itself, which may be punctured for use. Preferably the sealing means is a separate component which is constructed of, for example, high-density polyethylene, polypropylene, low-density polyethylene. Preferably, the sealing means is one which does not allow the container to be resealed. This is preferred to ensure patient compliance with the requirement that the solution be consumed within a short period of time, and also to minimize potential bacterial contamination once the container is opened. The geometry of the container is not critical, i.e., the container may have a square, rectangular or circular design. Of course, the design can be varied in a manner best to provide efficient packaging of the container in the kit.

The sealed container may be prepared, for example, using injection molding techniques well known to those skilled in the art. A particularly preferred sealed container used in this invention is formed by a blow molding process, well known to those skilled in the art, and immediately filled with sterilized buffered sucrose solution, followed by sealing the container.

The urine collection device provided in the kit of this invention must be capable of holding the volume of urine produced by the patient over a period of time ranging from about 3 hours to about 12 hours. Preferably, the device is a container or vessel. The preferred volume for the urine collection device is from about 500 ml to about 2600 ml. The most preferred volume is about 1600 ml. The material from which the device is made must also be chemically compatible with both human urine and with the preservatives optionally placed into the device. Suitable materials of construction include, for example, polyethylene, glass, high-density polyethylene, poly(ethylene terephthalate), and low-density polyethylene. The preferred materials are low-density polyethylene and high-density polyethylene, and the most preferred material is high-density polyethylene. The device preferably has a sufficiently wide base so that it is stable when resting on a surface. Preferably, the urine collection device has a handle with a sufficiently large opening to facilitate carrying the device in an upright position, and most preferably the handle is an integral part of the device. The opening in the handle is preferably sufficiently large to store the funnel therein. For an example of a particularly preferred embodiment of the urine collection device, see the drawing, wherein funnel 3 is shown to be storable in the open handle of the plastic container 2. The opening of the device is preferably skewed somewhat from the vertical to facilitate collection of urine. The opening is also preferably large enough to facilitate collection of urine; most preferably, the opening has a diameter of about 53 mm. A particularly preferred urine collection device may be prepared using injection molding techniques which are will known to those skilled in the art.

The urine collection device has a closure allowing the device to be sealed to prevent leakage or contamination of the urine collected therein. Suitable closures include a threaded cap which can be tightened onto a threaded lip of a container, a closure with a bayonet lock, and a plug. Materials of construction for the closure include, for example, polyethylene, high-density polyethylene, and polyvinyl chloride. Preferably, the closure is lined with a material softer than the closure material to facilitate formation of a seal between the closure and the container. The liner material may be present as a single layer, or as multiple layers. Suitable liner materials include, for example, polyethylene, low-density polyethylene, high-density polyethylene, and poly(tetrafluoroethylene). The most preferred liner comprises a layer of foamed low-density polyethylene between two layers of polyethylene. Optionally, a preservative may be placed in the urine collection device to stabilize the urine sample. The purpose of the preservative is to prevent growth of microorganisms which could potentially decrease the accuracy of the assay by degrading any sucrose present in the urine. Suitable preservatives include, for example, boric acid, sodium bisulfite fluoride, thymol, sodium azide, formaldehyde, chloroform, toluene, phenol. The preferred preservative is boric acid. The most preferred amount is 7.5 g, which is sufficient to stabilize 800 ml of urine, the average amount collected. Preferably, the preservative is in the form of a tablet, but a liquid or a powder may be added to the collection device as well. Other constituents of the tablet may include, for example, lactose, starch, and avicel.

Optionally, a collection funnel is included in the kit for use with the urine collection device. This funnel is adapted to be attached to the device to facilitate collection of urine and may be particularly designed for the convenience of female patients if desired. Preferably, this is accomplished by means of threads matching those on the device, so that the funnel may be attached to the device in the same manner as a threaded cap. Other possible means of attachment include a twist lock, bayonet lock, and a plug type attachment. Suitable materials of construction for the funnel include, for example, polypropylene, polyethylene, low-density polyethylene, and high-density polyethylene. The preferred materials are polypropylene, and high-density polyethylene, and the most preferred material is polypropylene.

In addition, the kit may optionally contain a lid for the funnel. The lid fits tightly over the top of the funnel, and when the funnel is attached to the device, the lid allows the device with the funnel in place to be sealed to prevent leakage or contamination of the urine contained therein. Suitable materials of construction for the lid include, for example, polypropylene, polyethylene, low-density polyethylene, and high-density polyethylene. The most preferred material is polypropylene. The preferred funnel and lid are described in copending U.S. patent application number 08/809,302, filed Mar. 14, 1997, the disclosure of which is incorporated by reference herein.

The kit may also include instructions for use of the kit. These instructions may describe the necessary fasting period prior to use, the manner of ingestion of the sucrose solution, use of the urine collection device, the collection period for urine, the submission of urine for testing, and any other information necessary for proper use of the kit by the patient. Any portable medium for transmitting these instructions may be employed, including an instruction card or pamphlet, a compact disc, audio tape, video tape, and a floppy disk. The preferred medium for the instructions is an instruction card or pamphlet.

The kit may also contain items to facilitate the opening of the beverage or assist in the consumption of the beverage or in the collection of the urine.

What is claimed is:

1. A kit for use in a method for detecting gastric damage in a patient; said kit comprising:
   (a) a sealed container of sterilized buffered aqueous sucrose solution for oral ingestion wherein the sealed container cannot be resealed after opening and wherein the sucrose solution has a pH in the range from about 6 to about 8; and
   (b) a urine collection device that is suitable for collection and storage of human urine, wherein the urine collection device has an open handle with a funnel storable in the open handle.

2. The kit of claim 1 wherein at least one compound which acts as a preservative is included in the urine collection device.

3. The kit of claim 2 wherein sucrose is present in the sucrose solution in a concentration in a range from about 15% to about 25% by weight of the solution.

4. The kit of claim 3 further comprising a collection funnel adapted to attach to the urine collection device.

5. The kit of claim 4 further comprising a lid which fastens to the collection funnel to form a closed vessel when the funnel is attached to the urine collection device.

6. The kit of claim 1 wherein sucrose solution has substantially free of microorganisms.

7. The kit of claim 6 further comprising instructions for use of the kit.

8. The kit of claim 7, wherein the sucrose solution is buffered with sodium phosphate, dibasic, in an amount from about 0.01% to about 0.4% by weight of the solution and citric acid in an amount from about 0.01% to about 0.4% by weight of the solution.

9. The kit of claim 8 wherein the urine collection device is comprised of polyethylene.

10. The kit of claim 9 wherein the preservative is boric acid.

11. The kit of claim 10 wherein the urine collection device has a volume of about 1600 ml.

12. The kit of claim 11 wherein the container is comprised of polyethylene.

13. The kit of claim 12 wherein the container has a volume of about 1600 ml.

14. The kit of claim 13 wherein the funnel is comprised of polypropylene.

15. The kit of claim 1 wherein the lid is comprised of polypropylene.

16. The kit of claim 15 wherein the sealed container contains a single dose of sucrose solution.

* * * * *